United States Patent
Yang et al.

(10) Patent No.: US 6,814,744 B2
(45) Date of Patent: Nov. 9, 2004

(54) BALLOON CATHETER WITH STRIPED FLEXIBLE TIP

(75) Inventors: Dachuan Yang, Hillsborough, NJ (US); Paul J. Miller, St. Paul, MN (US)

(73) Assignee: SciMed Life Systems, Inc, Maple Grove, MN (US)

( * ) Notice: Subject to any disclaimer, the term of this patent is extended or adjusted under 35 U.S.C. 154(b) by 201 days.

(21) Appl. No.: 09/965,765

(22) Filed: Sep. 28, 2001

(65) Prior Publication Data

US 2003/0065352 A1 Apr. 3, 2003

(51) Int. Cl.⁷ .............................................. A61M 29/00
(52) U.S. Cl. ...................................... 606/194; 606/191
(58) Field of Search ................................. 606/191, 192, 606/193–199; 623/1.11, 1.12

(56) References Cited

U.S. PATENT DOCUMENTS

| | | | |
|---|---|---|---|
| 5,047,045 A | 9/1991 | Arney et al. ................. 606/194 |
| 5,156,594 A | 10/1992 | Keith ........................... 604/96 |
| 5,484,424 A | 1/1996 | Cottenceau et al. ......... 604/282 |
| 5,549,552 A | 8/1996 | Peters et al. ................... 604/96 |
| 5,891,114 A | 4/1999 | Chien et al. ................. 604/282 |
| 5,897,537 A | 4/1999 | Berg et al. .................... 604/282 |
| 5,935,122 A | 8/1999 | Fourkas et al. .............. 604/523 |
| 5,938,653 A | 8/1999 | Pepin ........................... 604/527 |
| 5,976,120 A | 11/1999 | Chow et al. ................. 604/525 |
| 6,136,006 A | * 10/2000 | Johnson et al. ............. 623/1.12 |
| 6,159,187 A | 12/2000 | Park et al. ................... 604/264 |
| 6,187,130 B1 | 2/2001 | Berard et al. ................ 156/294 |
| 6,213,995 B1 | 4/2001 | Steen et al. .................. 604/527 |
| 6,245,053 B1 | 6/2001 | Benjamin .................... 604/523 |
| 6,503,353 B1 | * 1/2003 | Peterson et al. ............. 604/264 |
| 6,554,841 B1 | * 4/2003 | Yang ............................ 606/194 |
| 2001/0010247 A1 | 8/2001 | Snow ........................... 156/171 |
| 2002/0038140 A1 | * 3/2002 | Yang et al. .................. 623/1.12 |
| 2002/0038141 A1 | * 3/2002 | Yang et al. .................. 623/1.12 |

FOREIGN PATENT DOCUMENTS

| | | |
|---|---|---|
| EP | 0 618 059 A1 | 3/1994 |
| EP | 0 956 878 | 11/1999 |
| WO | 97/37713 | 10/1997 |

* cited by examiner

*Primary Examiner*—David O. Reip
*Assistant Examiner*—Jessica R. Baxter
(74) *Attorney, Agent, or Firm*—Vidas, Arrett & Steinkraus P.A.

(57) ABSTRACT

A distal tip for a catheter which is defined by a matrix and at least one stripe. The matrix is defined by at least one matrix material, and the at least one stripe is defined by at one stripe material. The predetermined hardness of the at least one stripe material has a greater durometer value than the predetermined hardness of the at least one matrix material.

13 Claims, 6 Drawing Sheets

BALLOON CATHETER WITH STRIPED FLEXIBLE TIP

CROSS-REFERENCE TO RELATED APPLICATIONS

Not Applicable

STATEMENT REGARDING FEDERALLY SPONSORED RESEARCH

Not Applicable

BACKGROUND OF THE INVENTION

This invention relates to the field of intravascular medical devices, and more particularly to the field of catheters such as angioplasty, neurological and guide catheters, among others, which may be used in various medical procedures such as percutaneous transluminal angioplasty (PTA), percutaneous transluminal coronary angioplasty (PTCA) as well as in procedures involving the placement of medicines and medical devices within the body. The present invention is directed to all forms of catheters which may be advanced through a body lumen or vessel. Some examples of catheters are over-the-wire (OTW) catheters, such as are described in U.S. Pat. No. 5,047,045; single-operator-exchange (SOE) balloon catheters, such as are described in U.S. Pat. No. 5,156,594 and U.S. Pat. No. 5,549,552. Other examples of catheters which may incorporate the unique features of the present invention are also described in U.S. Pat. No. 5,938,653, U.S. Pat. No. 5,897,537, among others.

The entire content of all of the patents listed within the present patent application are incorporated herein by reference.

Intravascular diseases are commonly treated by relatively non-invasive techniques such as PTA and PTCA. These angioplasty techniques typically involve the use of a balloon catheter. In these procedures, a balloon catheter is advanced through the vasculature of a patient such that the balloon is positioned proximate a restriction in a diseased vessel. The balloon is then inflated and the restriction in the vessel is opened. In other uses a catheter may be used to delivery an endoprosthesis such as a stent, graft, vena cava filter or other implantable device. Where an implantable device is to be delivered into a body lumen the catheter may include one or more inflatable portions or balloons.

Many procedures make use of a guide catheter positioned within the vascular system of a patient. The guiding catheter assists in transporting a balloon dilation catheter, or other form of treatment catheter, to the portion of the vessel requiring treatment or inspection. The guide catheter is urged through the vasculature of the patient until its distal end is proximate the restriction. The balloon catheter may then be fed through a lumen in the guide catheter.

Whether an individual procedure utilizes a guide catheter or simply requires the use of a solitary dilitation or medical device delivery catheter, catheters typically must possess a level of rigidity which will allow it to traverse tortious pathways through blood vessels in a manner that minimizes trauma. The catheter must be capable of being advanced through the vascular system without folding or buckling despite application of longitudinal and/or rotational forces upon the catheter. Because many catheters have the desired rigidity, it is desirable to incorporate a relatively flexible and desirably atraumatic tip on the distal end of the catheter to avoid injury to the walls of the blood vessels as the otherwise comparatively rigid catheter is advanced therethrough.

BRIEF SUMMARY OF THE INVENTION

The present invention provides a catheter with a novel tip or distal end which is sufficiently rigid to avoid kinking and bending as it advances through a lumen, but which is sufficiently soft and flexible such that the tip is less likely to cause trauma to vessel surfaces which it may contact.

The catheter tip may be provided with the desired characteristics by constructing the tip from a combination of at least two materials having different material characteristics such as hardness.

In at least one embodiment of the invention, the catheter tip comprises a first material or matrix and one or more stripes or segments of a second material, wherein the second material is harder than the first material.

As used herein, the term 'hardness' is used to define a differentiating feature between the first material and the second material. Hardness may be defined using the Shore scale of hardness wherein the second material may have a greater value on the Shore scale of hardness than that of the first material. However, the term 'hardness' as used herein may be used to denote a measurable difference between the first material and the second material other then that which may be indicated using a Shore hardness test. The hardness as defined by the Shore scale is considered to be a significant feature in differentiating between the first material and the second material, 'hardness' may also refer to concepts such flexibility, elasticity, tensile modulus, modulus of elasticity, as well as many other characteristics which may be different from one another.

The second material may be characterized as one or more stripes of material imbedded within or engaged to the first material. The stripes of material may be coextruded with the matrix or may be engaged to the matrix after formation of the first material. The stripes of the second material may be uniform in width along the length of the catheter tip. Alternatively the stripes may taper, be intermittent, or otherwise configured. Furthermore, the stripes may be disposed about the matrix in a variety of ways, such as for example, one or more stripes may be helically wound about the tip, multiple stripes may be longitudinally parallel throughout the length of the tip, a stripe or stripes may extend along the length of the tip and tapper toward or away from the end of the tip in increasing or decreasing width.

Other characteristics of the stripe or stripes of secondary material may also be varied relative to the first material matrix. For example, the second material may have a thickness equal to or different from the thickness of the first material.

The stripes of relatively hard secondary material may alternatively be characterized as one or more coatings applied to the surface of the first material.

The second material may also be characterized as one or more fibers or braids of fiber of a predetermined material or combination of materials. The fibers may be oriented relative to the longitudinal axis of the catheter tip in a variety of patterns. For example the fibers may be substantially parallel to the longitudinal axis of the angled relative thereto, helically or otherwise disposed thereabout, etc.

In at least one embodiment of the invention, the stripe(s) of second material may be disposed about the inside and/or outside of the catheter tip.

In yet another embodiment of the invention, the stripes of a second material may be fully enclosed, or "sandwiched" within the matrix of the first material.

In still another embodiment of the invention the matrix of the catheter tip, i.e. the first material, may itself be comprised of a variety of materials. In such an embodiment the stripe(s) may be enclosed between an inside layer of material and an outside layer of material, wherein the inside material and the outside material are different from one another. In such an embodiment the stripe(s) of second material remain harder than the combined layers of first material.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

In the various FIGS. 1–13 identical components are designated by the same reference numbers in the following description of various embodiments.

Figure 1:
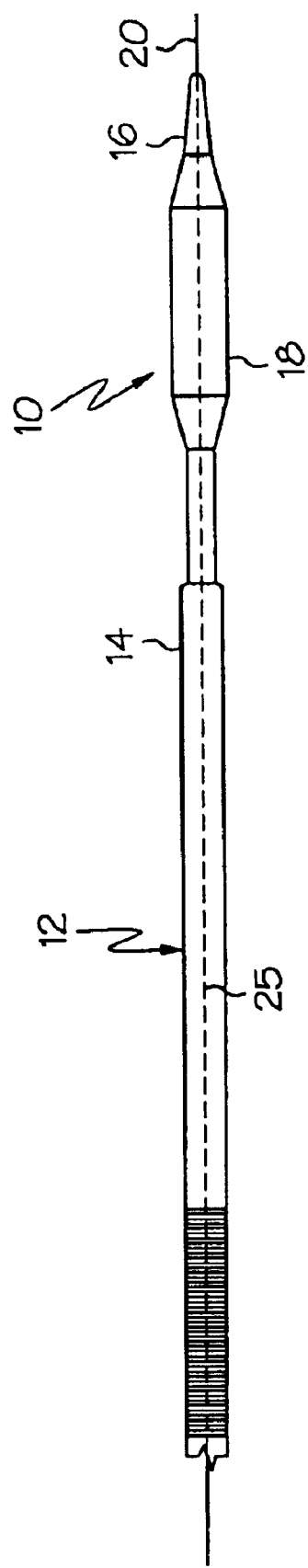
FIG. 1 is a side view of an embodiment of the invention wherein the tip is shown on a typical catheter.

As may be seen in FIG. 1, the present invention may be embodied in a catheter, indicated generally at 10. Catheter 10, may be any type of catheter such as a balloon catheter, a stent delivery catheter, a guide catheter or other type. The catheter may have a fixed wire, OTW, rapid exchange or other type of configuration as desired. The catheter 10 has a body 12 consisting of a shaft 14 which extends distally to a distal end or tip 16. In many embodiments the catheter 10 may include an inflation member or balloon 18 disposed about the shaft 14 proximal to the distal tip 16. The inflation member may be configured to deliver or seat a medical device such as a stent and may be equipped with one or more stent retaining sleeves, such as is described in U.S. application Ser. No. 09/829,295 to Yang, filed Apr. 9, 2001, the entire contents of which being incorporated herein by reference.

As indicated above, catheter 10 may be any type of catheter capable of being inserted into and advanced through a body lumen. FIG. 1 shows a typical catheter 10 which is advanced through the body along a guide wire 20. In order for guide wire 20 to pass through the catheter 10, the catheter or at least a portion thereof, defines a lumen 25 through which the guide wire 20 or other object may be advanced. Where the catheter 10 is a guide catheter, lumen 25 may have significant diameter to allow a second catheter (not shown) to be advanced through the lumen 25.

In the embodiment shown, the end 24 of the distal tip 16 of catheter 10 includes a distal opening 22 (shown in FIG. 2) through which the guide wire 20 passes out of the lumen 25. As suggested above, the size of the opening 22 may be varied. For example, where the catheter 10 is a guide catheter, the opening 22 may have a diameter sufficient to allow a dilitation catheter or other type of catheter to pass therethrough. In some alternative embodiments, the opening and lumen may be absent from the tip 16.

Figure 2:
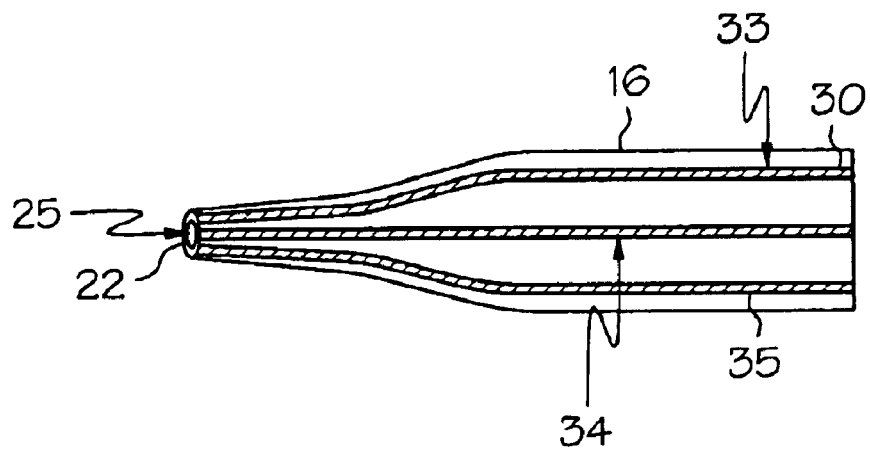
FIG. 2 is a close up side view of an embodiment of the invention.

In FIG. 2 a close up view of an embodiment of the tip 16 is shown. The tip 16 has a unique construction which allows the tip to remain functionally rigid so that the catheter 10 may be advanced through a vessel but which is also soft and flexible to help prevent potential damage to the vessel wall as the catheter is advanced. The improved unique physical characteristics of the tip 16 are the result of the unique composite construction of the tip 16 which includes a combination of a matrix 33 composed of a first material 30, and one or more stripes 35 composed of a stripe material 34.

The matrix material 30 may have a hardness value which on the Shore durometer scale is less than the hardness value of the stripe material 34. The matrix material 30 is formed into a generally tubular body 32 which provides the tip 16 with its shape as well as its inside surface 100 and outside surface 102 such as may be seen in FIGS. 9–10 and 12.

In the various embodiments shown in FIGS. 2–13, the tip 16 is shown to include a matrix 33 and one or more strips 35. It should be noted however, that the present invention is not limited to only the tip 16 of the catheter 10 such as is shown in FIG. 1. As it may be desirable to provide additional portions of the catheter 10 with the unique physical properties of the invention, it is understood that the entire catheter 10 or portions thereof in addition to the tip 16 may be provided with the combination of materials described herein.

The matrix material 30 may be any elastomer material known which has a hardness as measured by a Shore D durometer of about 64D. In some embodiments the hardness of the first material 30 may be between about 25D to about 74D. In still some other embodiments the hardness of the first material 30 may be about 30D to about 65D. The stripe material 34 may be any material having a durometer hardness of about 55D to about 84D. In at least one embodiment of the invention the matrix material 30 has a hardness of 55D and the stripe material 34 has a hardness of 80D.

In the various embodiments shown, the combination of matrix 33 and the comparatively hard stripes 35 provides the tip 16 with improved flexibility for negotiating the tortious confines of the vasculature but also with improved longitudinal rigidity for advancing the tip 16 with improved pushability. As an example of the improved characteristics of the tip 16, in at least one tested embodiment, tip 16 has performance characteristics similar to a 74A rubber for purposes of radial expansion, and 60D for purposes of longitudinal elongation.

An additional benefit provided by the unique hybrid construction of tip 16 is that when the catheter 16 is used with a guide wire 20, the harder stripes 35 restrict the elasticity of the matrix 33 such that when the tip 16 travels along the guide wire 20 or when another catheter is passed through the opening 22, the tip 16 remains longitudinally rigid but is able to expand radially to allow for improved passage of the wire and/or catheter therethrough.

Figure 9:
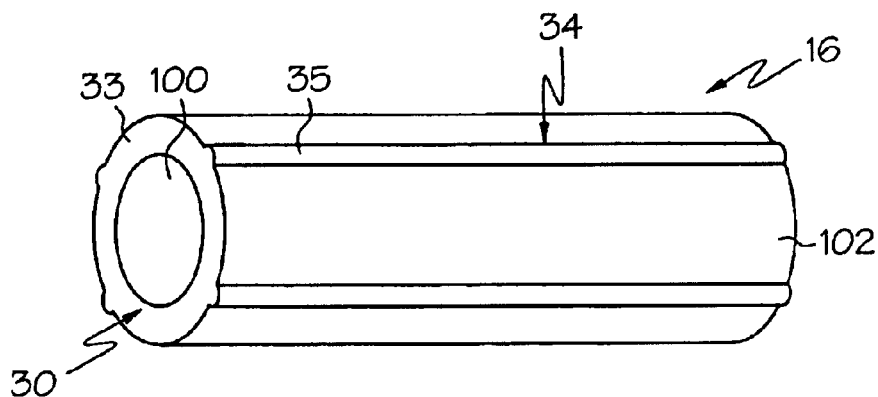
FIG. 9 is a perspective view of another embodiment of the catheter tip of the present invention.
Figure 10:
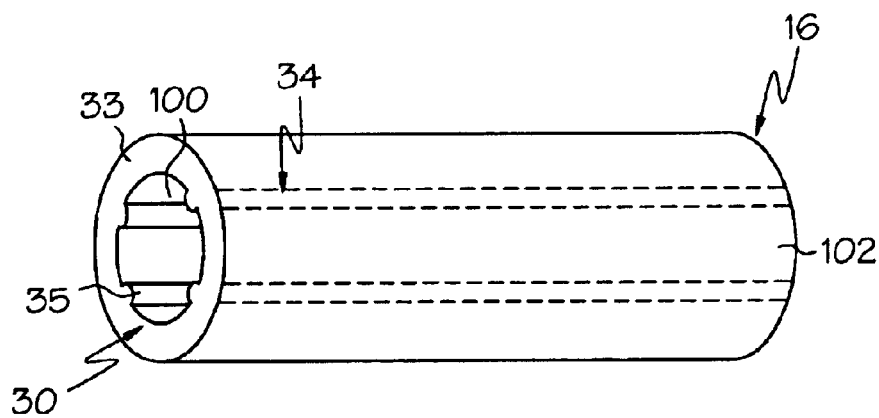
FIG. 10 is a perspective view of another embodiment of the catheter tip of the present invention.
Figure 11:
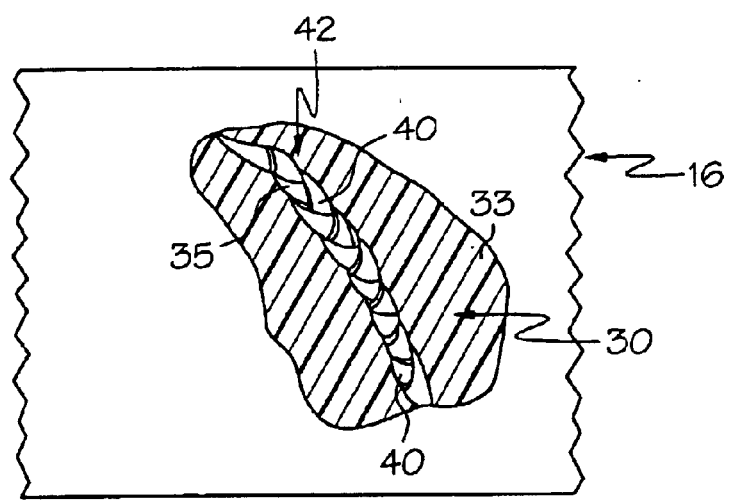
FIG. 11 is a detailed partially cut-away view of another embodiment of the catheter tip of the present invention.

In the various embodiments show and described herein, the number of stripes 35 may vary from a single stripe 35 such as may be seen in FIG. 11 to several stripes as shown in FIGS. 2–10 and 12–13. In FIGS. 2–10 it may be seen that the stripes 35 may have a wide variety of orientations and positions relative to the matrix 33. The embodiments depicted in FIGS. 2–10 are just several examples of the configurations which may be utilized. One of skill in the art will recognize that the present invention is also directed to all other configurations, orientations and numbers of strips 35 which may be utilized with the matrix 33.

In FIG. 2, the stripes 35 appear to be a surface feature applied to the matrix 33. However, the stripes 35 may be partially imbedded within the matrix 33 or may share the same thickness as the matrix 33. The stripes 35 may be a braid of multiple fibers of hardened material 34 or may be a coating of hardened material 34. In the embodiment shown the stripes 35 are uniformly distributed about the circumference of the tip 16, however other dispersement patterns are possible, examples of which are described in greater detail below. The stripes also extend the entire length of the tip 16 and may be configured to gradually reduce in width as they taper toward the end 24. Such a configuration allows for uniform distribution of the first material 30 and second material 34 through out the length of the tip 16. However, if it is desired to provide a tip 16 with an end 24 which is harder or softer than the remaining portion of the tip 16, the width of the stripes 35 may be increased or reduced respectively.

Figure 3:
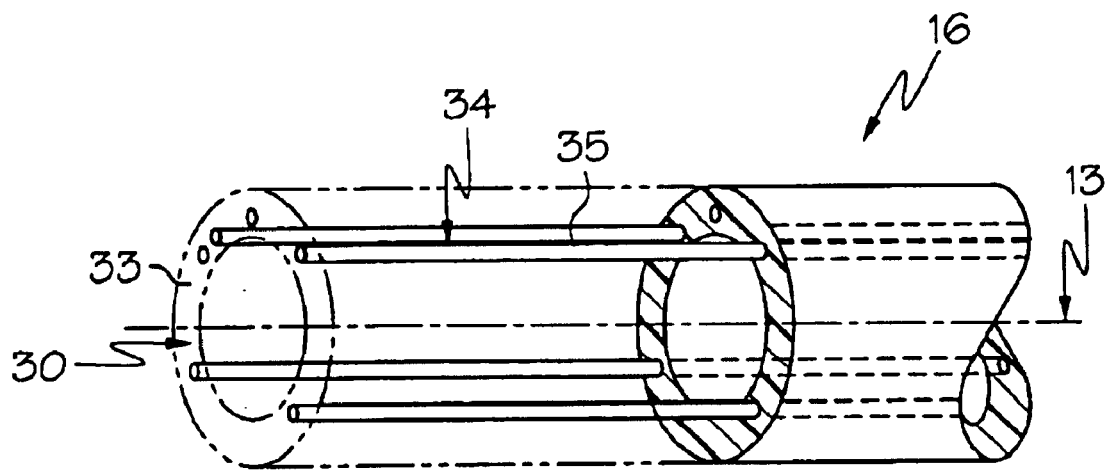
FIG. 3 is a partial cut-away perspective view of an embodiment of the catheter tip of the present invention.

In FIG. 3, the stripes 35 are imbedded within the matrix 33 and extend the entire length of the tip 16. In the present embodiment, prior to being mounted on the stent delivery catheter the stripes 35 are oriented within the matrix 33 to be parallel to the longitudinal axis 13 of the tip 16.

Figure 4:
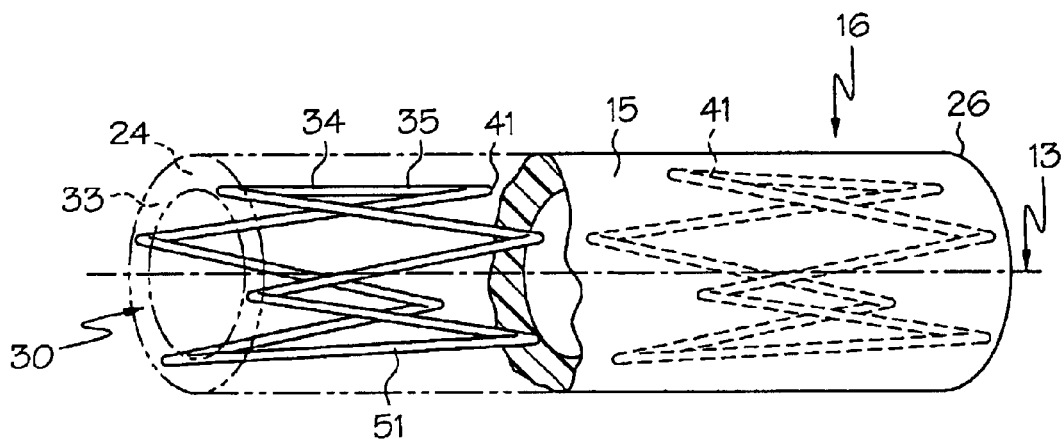
FIG. 4 is a partial cut-away perspective view of another embodiment of the catheter tip of the present invention.

In the embodiment shown in FIG. 4, a pair of stripes 35 are configured within the matrix 33 in opposing zig-zag patterns. The stripes 35 extend from a respective end 24 or 26 of the tip 16 and extend to a middle portion 15 of the tip 16 and then extend back toward the opposing end in an alternating pattern. In the embodiment shown, the zig-zag configured stripes 35 may be made up of individual members 51 whose ends are adjacent to one another. Alternatively, a single zig-zag stripe 35 may be employed which is a continuous stripe having a plurality of folds 41 at the tip ends 24 and 26 to provide the pattern shown.

Figure 5:
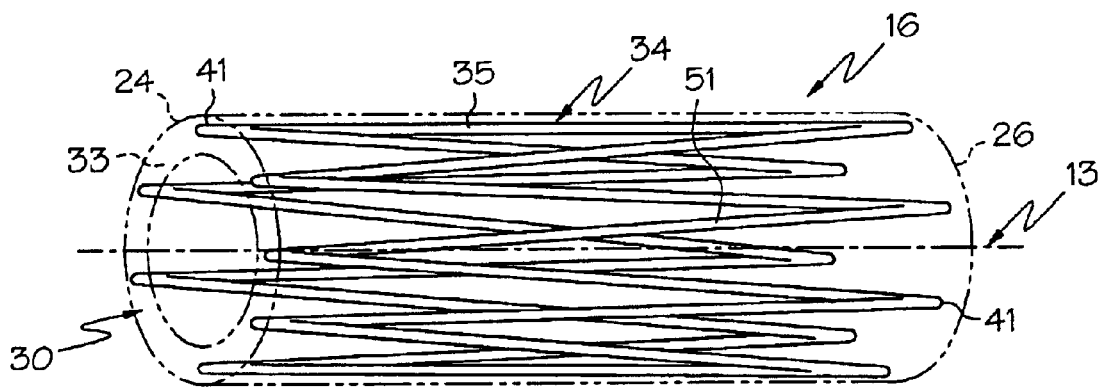
FIG. 5 is a partial cut-away perspective view of another embodiment of the catheter tip of the present invention.

In FIG. 5, the stripes 35 are also in a zig-zag pattern. The stripe 35 (or members 51 thereof) are angularly disposed relative to the longitudinal axis 13 of the tip 16. However, in FIG. 5 the stripes 35 (or lengths 51 thereof) fully extend from one end 24 of the tip 16 to the other 26.

Figure 6:
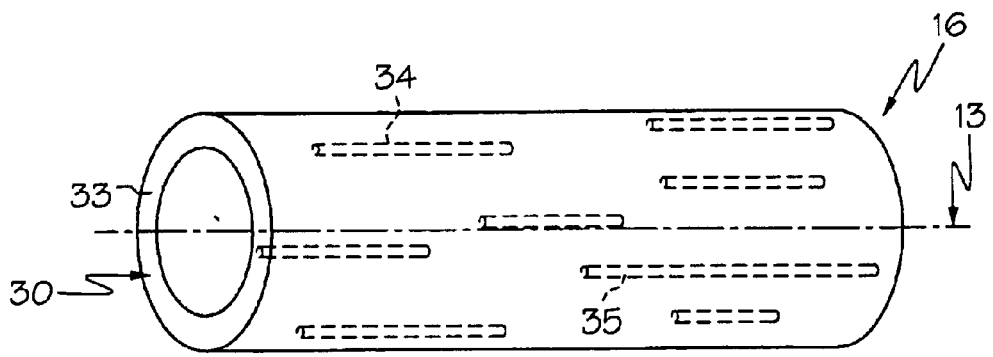
FIG. 6 is a partial cut-away perspective view of another embodiment of the catheter tip of the present invention.

In FIG. 6, an embodiment of the tip 16 is shown wherein each of the plurality of stripes 35 have a random length which may or may not extend the entire length of the tip 16. Additionally, the individual stripes 35 may or may not be parallel to the longitudinal axis 13, and may have a completely random orientation relative to the longitudinal axis 13. It should also be noted that the stripes 35 may or may not be arranged in a uniform pattern such as is shown in the previously described embodiments.

Figure 7:
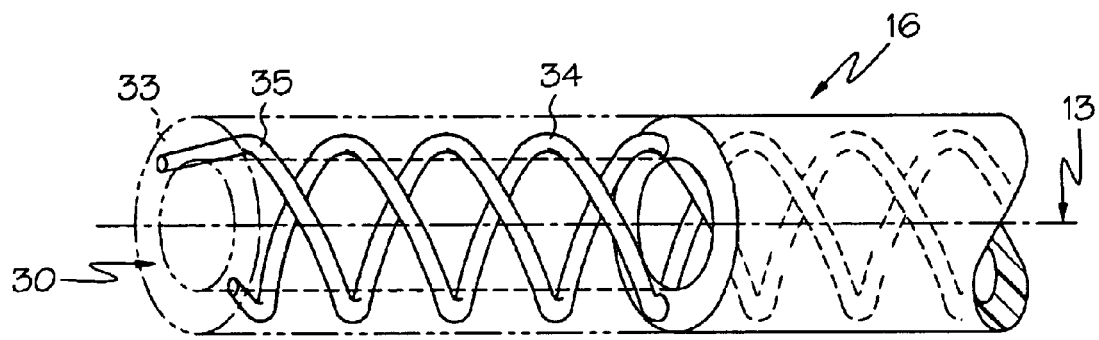
FIG. 7 is a partial cut-away perspective view of another embodiment of the catheter tip of the present invention.
Figure 8:
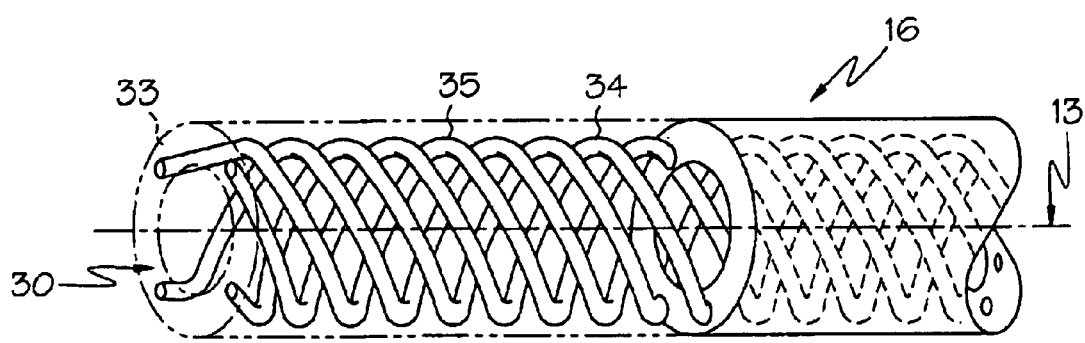
FIG. 8 is a partial cut-away perspective view of another embodiment of the catheter tip of the present invention.

In FIG. 7, a pair of strands 35 are shown in a double helix configuration wherein each strand 35 is helically disposed relative to the longitudinal axis 13 in opposing directions. In the embodiment shown in FIG. 8 a plurality of helically disposed strands 35 are imbedded in the matrix 33, wherein each of the strands 35 is oriented in the same direction.

In FIGS. 9–10 embodiments of the tip 16 are shown wherein the stripes 35 need not be completely imbedded within the matrix 33. In FIG. 9, the stripes 35 are engaged to the inner surface 100 of the matrix 33, whereas in FIG. 10 the stripes 35 are engaged to the outer surface 102 of the matrix 33. Whether engaged to the inside 100 or outside surface 102, the matrix 33 may partially surround the stripes 35. Alternatively or in addition, the stripes 35 may be secured to the respective surface 100 and 102 in a variety of manners. For example, chemical adhesives, heat welding by laser or other means, chemical welding, etc, or other securing methods may all be used to secure the stripes 35 to the respective surfaces 100 and 102 of the matrix 33. However, in a preferred embodiment, the matrix material 30 and the stripe material 34 are coextruded. It should also be noted that in an alternative embodiment one or more stripes may be engaged to the inner surface of the matrix, the outer surface of the matrix, and/or imbedded within the matrix or any combination thereof. Regardless of the position of the stripes within the matrix or on of its surfaces, the stripes may be positioned in any of the variety of configurations and orientations described herein.

In any of the embodiments described and/or depicted herein, the matrix material 30 may be selected from a wide variety of substances. For example, the matrix may include but is not limited to, one or more of the following substances: soft grade polyester/polyether elastomers such as Arnitel™ available from DSM Engineering, polyurethane-polyether polymers, such as Tecothane™ available from Thermedics, Inc.; polyester-polyurethanes, such as Pellethane™ sold by Dow Chemical; polyester-polyurethanes, such as Estane™ sold by BF Goodrich; polyether block amides (PEBA), such as Pebax™ available from Elf Atochem; and styrene-butadien-styrene triblock copolymers such as Kraton™ sold by Shell Chemical company. Other materials which may also be used in the production of the matrix material 30 include, but are not limited to styrenic block copolymers, polyurethanes, silicone rubber, natural rubber, copolyesters, polyamides, EPDM rubber/polyolefin, nitril rubber/PVC, fluoroelastomers, butyl rubber, epichlorohydrin, soft block copolymers, and any combinations thereof.

The stripe material 34 may also be selected from a wide range of materials. For example the stripe material 34 may be include, but is not limited to, one or more of the following substances: polyethylene terephthalate (PET), polyethylene naphthalate (PEN) polybutylene terephthalate (PBT), polytrimethylene terephthalate (PTT), engineering thermoplastic polyurethanes, fluoropolymers, polyester/polyether elastomers such as Arnitel™ available from DSM Engineering, polyurethane-polyether polymers, such as Tecothane™ 1055D or 1075D, Tecoplast™ 470 both of which are available from Thermedics, Inc.; polyester-polyurethanes, such as Estane™ 58170 sold by BF Goodrich; polyether block amides (PEBA), such as Pebax™ 7233 or 6333 both of which are available from Elf Atochem. Other materials which may also be used in the production of the stripe material 34 include, but are not limited to: polyolefins, polystyrene, polyvinyl chloride, acrylonitrile-butadiene-styrene polymers, polyacrylonitrile, polyacrylate, vinyl acetate polymer, cellulose plastics, polyurethanes, polyacetal, polyethers, polycarbonates, polyamides, polyphenylene sulfide, polyarylethersulfones, polyaryletherketones, polytetrafluoroethylene, polyamide copolymer, such as MXD6™ availible from Mitsubishi Gas Chemical Co., or Cristamid™ availible from Atofina and any combinations thereof.

The above examples of the matrix and stripe materials 30 and 34 respectively, are in no way exhaustive of the potential substances or combinations of substances which may be used. For example, the matrix 30 and/or stripe material 34 may incorporate a radiopaque substance to provide the tip 16 with improved radiopacity when advanced through the body. The present invention is directed to a distal tip 16 or other portion of a catheter composed of any materials which have the qualities previously described for the respective materials 30 and 34.

The tip 16 may be embodied in a wide range of striped configurations. As may be seen in FIG. 11, the stripes 35 themselves may also be provided in a variety of designs. In FIG. 11, a close-up view of a stripe 35 is shown within the surrounding matrix 33. The stripe 35 is made up of a plurality of interwoven fibers 40 which are woven together to form a braid structure 42. The braided configuration of the stripe 35 provides the tip 16 with a stripe or stripes 35 that may be substantially stronger than a single monofilament fiber 40, while maintaining the desired hardness and flexibility characteristics of the stripe material 34. As a result, tip 16 with one or more braids 42 of a given stripe material 34 shown will have improved longitudinal strength characteristics without a reduction in flexibility which may have resulted if a harder material 34 were used to form a monofilament stripe. In addition, where the stripe 35 is a braid 42 of several fibers 40, the individual fibers may be materials having different characteristics.

Figure 12:
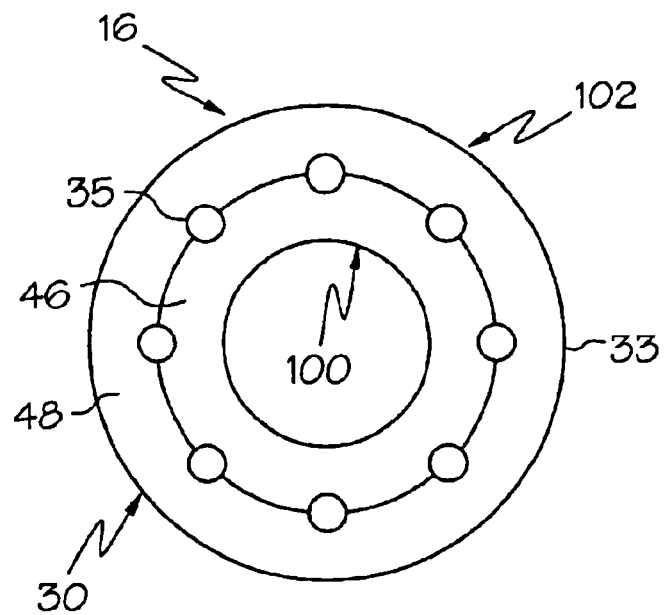
FIG. 12 is a cross-sectional view of another embodiment of the catheter tip of the present invention.

Not only are the stripes 35 variable in their characteristics, but the matrix 33 may also be provided in alternative forms. In FIG. 12, an embodiment of the tip 16 is shown wherein the matrix material 30 is actually a combination of materials. In the embodiment shown, the matrix 33 is a combination of an inner material 46 and an outer material 48, with a plurality of stripes 35 sandwiched in between. Providing the matrix 33 with a combination of materials may provide the tip 16 with even greater flexibility without substantial reductions in push-ability. For example, the inner material 46 may be a layer of hydrophobic elastomer such as a Siloxane-Polyurethane copolymer which has a relatively low surface friction and less tack, thereby providing the tip 16 with a reduced frictional interface between the inner surface 100 and a guide wire or catheter passing thereagainst. The outer material 48 may be comprised of a hydrophilic elastomer, such as hydrophilic polyurethane, which may provide the outer surface 102 of the tip 16 with wet lubricity characteristics when the outer surface is in contact with bodily fluids, such as when the catheter is advanced through a vessel. In addition to the example provided, it should be noted that the inner material 46 and the outer material 48 of the tip 16 may be provided with a wide variety of different or similar material combinations.

Figure 13:
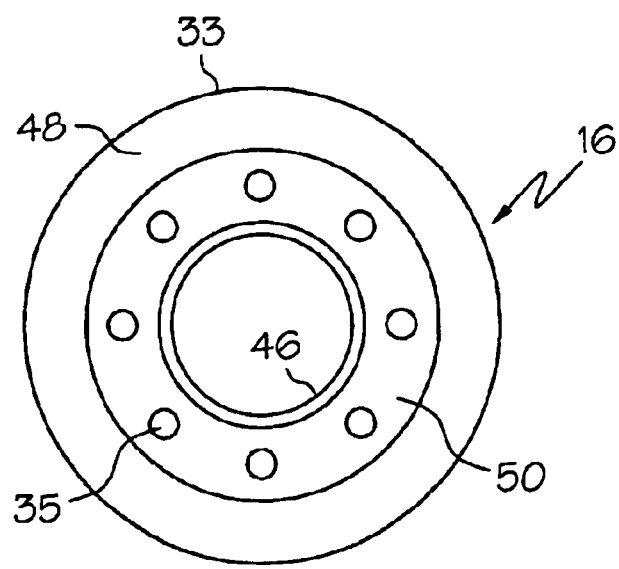
FIG. 13 is a cross-sectional view of another embodiment of the catheter tip of the present invention.

In FIG. 13 another embodiment is shown wherein the matrix 33 is comprised of three layers, with the stripes 35 completely imbedded within an intermediate layer 50, which is in turn sandwiched between the outer material 48 and inner material 46. Such an embodiment may be useful when the materials selected for the outer material 48 and inner material 46 do not tend to readily bond together and an intermediate material 50 is used to provide a material which the outer material 48 and inner material 46 may be more readily bonded to. The matrix 33 is not limited to only the one, two or three layer configurations described herein, but may be embodied in a wide range of configurations having a plurality of layers of one or more materials.

The tip 16 may be provided in a wide range of shapes and sizes. The tip may have surface features such as dimples or troughs, or may have structural alterations such as through holes or ports, for altering the retraction characteristics of the tip. Tip 16 may include additional layers such as internal or external coatings, such as may be known in the art for improving the tip's as well as the catheter's performance.

In addition to being directed to the specific combinations of features claimed below, the invention is also directed to embodiments having other combinations of the dependent features claimed below and other combinations of the features described above.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 2; claim 5 may be taken as alternatively dependent on claim 3, claim 6 may be taken as alternatively dependent from claim 3; claim 7 may be taken as alternatively dependent from claims 3, 5 or 6; etc.).

What is claimed is:

1. A catheter comprising:
   a tubular catheter shaft, the tubular catheter shaft having a proximal portion and a distal portion, the distal portion having a distal tip engaged thereto, the distal tip having a different material composition than the catheter shaft, the distal tip comprising an inner matrix layer, an outer matrix layer and at least one stripe positioned between at least a portion of the inner matrix layer and the outer matrix layer, the at least one stripe being substantially parallel to a longitudinal axis of the distal tip, the inner matrix layer defined by at least one inner matrix material and the outer matrix layer defined by at least one outer matrix material different form the inner matrix material, and the at least one stripe defined by at least one stripe material, the at least one inner matrix material and at least one outer matrix material each having a predetermined hardness and the at least one stripe material having a predetermined hardness, the predetermined hardness of the at least one stripe material having a greater durometer value than the predetermined hardness of the at least one inner matrix material and at least one outer matrix material.

2. The catheter of claim 1 wherein the tubular catheter shaft an the distal tip define a common lumen.

3. The catheter of claim 1 wherein the least one stripe has a length substantially equal to that of the matrix.

4. The catheter of claim 1 wherein the at least one stripe is a plurality of stripes.

5. The catheter of claim 4 wherein each of the plurality of stripes is distributed between the inner matrix layer and the outer matrix layer in a uniform manner.

6. The catheter of claim 4 wherein each of the plurality of stripes has a uniform orientation relative to the longitudinal axis of the distal tip.

7. The catheter of claim 1 wherein the inner matrix layer has an outside surface, the at least one stripe being engaged to the outside surface of the inner matrix layer.

8. The catheter of claim 1 wherein the at least one inner matrix material and the at least one outer matrix material are each selected from as least one member of the group consisting of polyester/polyether elastomers, polyurethane polyether polymers, polyester-polyurethanes, polyester-polyurethanes, polyether block amides (PEBA), styrene-butadien-styrene triblock copolymers, styrenic block copolymers, polyurethanes, silicone rubber, natural rubber, copolyester, polyamides, EPDM rubber polyolefin, nitril rubber/PVC, fluoroelastomers, butyl rubber, epichlorohydrin, soft block copolymers, end any combinations thereof.

9. The catheter of claim 1 wherein the at least one stripe material is selected from at least one member of the group consisting of polyethylene terephthalate (PET), polyethylene naphthalate (PEN), polybutylene terephthalate (PBT), polytrimethylene terephthalate (PTT), engineering thermoplastic polyurethanes, fluoropolymers, polyester/polyether elastomers, polyurethane polyether polymers, polyester-polyurethanes, polyether block amides (PEBA), polyolefins, polystyrene, polyvinyl chloride, acrylonitrile-butadiene-styrene polymers, polyacrylonitrile, polyacrylate, vinyl acetate polymer, cellulose plastics, polyurethanes, polyacetal, polyethers, polycarbonate, polyamides, polyphenylene sulfide, polyarylethersulfones, polyaryletherketones, polytetrafluoroethylene, polyamide copolymer, and any combination thereof.

10. The catheter of claim 1, wherein the at least one inner matrix material and the at least one outer matrix material each have a durometer hardness value in a range of about 25D to about 74D, and the at least one stripe material has a durometer hardness value in a range of about 55D to about 84D.

11. The catheter of claim 10 wherein the at least one inner matrix material and the at least one outer matrix material each have a durometer hardness value of about 55D, and the at least one stripe material has a durometer hardness value of about 80D.

12. The catheter of claim 1 wherein the catheter is selected from the group consisting of dilatation catheters, guide catheters, over-the-wire catheters, rapid exchange catheters, single-operator-exchange catheter, medical device delivery catheter, and any combinations thereof.

13. The catheter of claim 1 wherein at least a portion of the distal tip is radiopaque.

* * * * *